United States Patent [19]
Manz

[11] Patent Number: 6,123,858
[45] Date of Patent: *Sep. 26, 2000

[54] SLOW SAND FILTER FOR USE WITH INTERMITTENTLY FLOWING WATER SUPPLY AND METHOD OF USE THEREOF

[75] Inventor: David H. Manz, Calgary, Canada

[73] Assignee: University Technologies International Inc., Calgary, Canada

[*] Notice: This patent is subject to a terminal disclaimer.

[21] Appl. No.: 09/168,864

[22] Filed: Oct. 9, 1998

Related U.S. Application Data

[63] Continuation-in-part of application No. 08/788,497, Jan. 28, 1997, Pat. No. 5,993,672, which is a continuation-in-part of application No. 08/509,628, Jul. 31, 1995, abandoned, which is a continuation-in-part of application No. 08/141,598, Oct. 27, 1993, abandoned.

[51] Int. Cl.$^7$ .................................................. B01D 37/04
[52] U.S. Cl. ........................... 210/744; 210/104; 210/143
[58] Field of Search ..................................... 210/744, 807, 210/86, 104, 143, 289, 291, 456, 272, 290

[56] References Cited

U.S. PATENT DOCUMENTS

| | | | |
|---|---|---|---|
| 3,547,816 | 12/1970 | Horiguchi et al. ....................... | 210/272 |
| 3,817,378 | 6/1974 | Ross ........................................ | 210/274 |
| 4,765,892 | 8/1988 | Hulbert et al. .......................... | 210/290 |
| 5,032,261 | 7/1991 | Pyper ...................................... | 210/137 |

OTHER PUBLICATIONS

Visscher et al., "Slow Sand Filtration for Community Water Supply", Technical Paper No. 24, International Reference Centre for Community Water Supply and Sanitation, The Hague, The Netherlands, 198, p. 31.

Huisman, "Slow Sand Filtration", World Health Organization, Geneva, 1974, p. 32.

Buzunis, "Intermittently Operated Slow Sand Filtration: A New Water Treatment Process", Dept. of Civil Engineering, The University of Calgary, Mar. 1995, 220 pgs.

*Primary Examiner*—Ivars Cintins
*Attorney, Agent, or Firm*—Oyen Wiggs Green & Mutala

[57] ABSTRACT

This invention relates to a novel intermittent slow sand filter and a method of using the intermittent filter. More particularly, this invention pertains to a novel slow sand filter which remains effective, even when intermittently operated, and which can be periodically cleaned without disturbing the action of the intermittent filter. A slow sand filter apparatus comprising: a container having an upper portion and a lower portion; a water inlet in the upper portion of the container, the water inlet being connected to a supply of water; a filter material filling at least the lower portion of the container, the filter material having a top surface below the water inlet; a schmutzdeuke layer on the top surface of the filter material; a water outlet in the lower portion of the container below the top surface of the filter material; and a water level maintenance device in the upper portion which maintains water in the upper portion of the container at a maintenance level above the top surface of the filter material, the maintenance level being a balance between (1) a water maintenance level that is sufficiently deep that water falling from the water inlet onto the top of the water in the container does not significantly disturb the schmutzdeuke layer; and (2) a water maintenance level that is sufficiently shallow that oxygen from the air above the water level can diffuse through the water and reach the schmutzdeuke layer so that the schmutzdeuke layer is maintained in living condition even when there is no flow of water through the water inlet.

17 Claims, 9 Drawing Sheets

SLOW SAND FILTER FOR USE WITH INTERMITTENTLY FLOWING WATER SUPPLY AND METHOD OF USE THEREOF

This application is a continuation-in-part of application Ser. No. 08/788,497, filed Jan. 28, 1997, now U.S. Pat. No. 5,993,672, which was a continuation-in-part of application Ser. No. 08/509,628, filed Jul. 31, 1995, now abandoned, which was a continuation-in-part of application Ser. No. 08/141,598, filed Oct. 27, 1993, now abandoned.

FIELD OF THE INVENTION

This invention relates to a novel intermittent slow sand filter and a method of using the intermittent filter. More particularly, this invention pertains to a novel slow sand filter which remains effective, even when intermittently operated, and which can be periodically cleaned without disturbing the action of the intermittent filter.

BACKGROUND OF THE INVENTION

Slow sand filters are known to be effective in removing bacteria, parasites, *Giardia cysts, Cryptosporidium oocysts* and viruses. While bacteria, parasites and viruses may be killed or rendered inactive with disinfection, dormant cysts and oocysts are very resistant to disinfection unless disinfectant is administered very intensively. Slow sand filters may be used to supply clean water directly for consumption or may be used to supply water for further treatment, such as by reverse osmosis and ultra-filtration, both of which processes require quite clean water to begin with.

In the prior art, slow sand filters are known that require a continuous water supply, and that are intended for use with continuously flowing water. Such a prior art slow sand filter is described in U.S. Pat. No. 5,032,261, to Pyper. The slow sand filter includes a container partially filled with sand. The slow sand filter is provided with a water inlet and water outlet. Water containing oxygen continuously flows through the sand at a rate of about or slightly over 0.08 m/hour, with the sand providing a filter effect for the flowing water. In addition, when the sand is immersed in the oxygen containing flowing water for several days, a beneficial aerobic initially barely visible biolayer forms at the top of the sand. This layer is referred to as a schmutzdeuke, which is formed from various organisms such as algae, plankton, diatoms, protozoa and bacteria. The schmutzdeuke entraps and partially digests and breaks down organic matter contained in the raw water continuously passing through the filter. The organic matter accumulates on the schmutzdeuke and simple inorganic salts are formed. At the same time, inert suspended particles in the raw water are removed mechanically by the sand.

Such slow sand filters are not, however, effective where the water supply is intermittent, such as at country cottages. In such cases, the water in prior art slow sand filters becomes stagnant (loses oxygen) and the schmutzdeuke dies due to lack of oxygen. This shortcoming limits the utility of prior art slow sand filters.

U.S. Pat. No. 4,765,892, Aug. 23, 1988, Hulbert et al., discloses a slow sand filtering system in which an uncovered filter tank has therein a layer of sand, and an effective filter-enhancing amount of zeolite. The zeolite is topped by a growth of schmutzdeuke, with the schmutzdeuke comprising a layer of living organisms selected from the group consisting of algae, plankton, diatoms, protozoa, rotifers and bacteria.

Thus, in Visscher et al., "Slow Sand Filtration for Community Water Supply", Technical Paper No. 24, International Reference Centre for Community Water Supply and Sanitation, The Hague, The Netherlands, 1987, at page 31, it is stated that intermittent operation of slow sand filters should not be permitted because "it has been shown conclusively that an unacceptable breakthrough of bacteriological pollutants occurs four to five hours after the filters recommence operation". Likewise, Huisman, "Slow Sand Filtration", World Health Organization, Geneva, 1974, at page 32, teaches that slow sand filters should be operated at as constant a filtration rate as possible. Thus the understanding in the art was that slow sand filters should not be operated intermittently. By intermittently, it is not meant that the slow sand filter be occasionally taken out of operation for maintenance, such as is described in U.S. Pat. No. 4,765,892 of Hulbert, but that the slow sand filter remains in operation, with the schmutzdeuke alive, during the period when there is no flow of water through the filter. By contrast with the present invention, the filter of Hulbert is cleaned during maintenance, so that the schmutzdeuke does not remain alive until it is operated again.

For a slow sand filter of the type described by Hulbert, with depth of water above the filter material being in the range of 60 cm to 2.44 m, the schmutzdeuke will begin to die immediately as the water flow is shut off during periods of intermittent operation and will die overnight due to lack of oxygen. This can be shown from theoretical calculations of the oxygen demand of the schmutzdeuke.

SUMMARY OF INVENTION

The invention is directed to a slow sand filter apparatus comprising: a container having an upper portion and a lower portion; a water inlet in the upper portion of the container, the water inlet being connected to a supply of water; a filter material filling at least the lower portion of the container, the filter material having a top surface below the water inlet; a schmutzdeuke layer on the top surface of the filter material; a water outlet in the lower portion of the container below the top surface of the filter material; and a water level maintenance device in the upper portion which maintains water in the upper portion of the container at a maintenance level above the top surface of the filter material, the maintenance level being a balance between (1) a water maintenance level that is sufficiently deep that water falling from the water inlet onto the top of the water in the container does not significantly disturb the schmutzdeuke layer; and (2) a water maintenance level that is sufficiently shallow that oxygen from the air above the water level can diffuse through the water and reach the schmutzdeuke layer so that the schmutzdeuke layer is maintained in living condition even when there is no flow of water through the water inlet.

The slow sand filter apparatus can include a diffuser above he water maintenance level, water from the water inlet passing through the diffuser before reaching the top of the water maintenance level and the underlying filter material.

The water level maintenance device can include a pipe connected to the water outlet and extending upward to the water maintenance level. The water level maintenance device can maintain the water level between about 1 cm and 8 cm above the top of the filter material or between about 1 cm and 5 cm above the top of the filter material. The filter material can be quartz sand. The slow sand filter apparatus can include a water inlet line connected to the water inlet and water inlet control means for controllably supplying water to the water inlet line.

The slow sand filter apparatus can include a first water level detector to detect an upper water level in the container;

a second water level detector to detect a lower water level in the container; and a controller connected to receive signals from the first and second container water level detectors and to provide signals to the water inlet control means, so that the water maintenance levels are maintained within the desired range of water maintenance levels.

The slow sand filter apparatus can further comprise a high water level detector connected to provide a signal to the controller indicative of excessively high water level in the container.

The diffuser can include discrete holes which can allow water accumulating above the diffuser to percolate down through the diffuser onto the top of the water in the container.

The slow sand filter apparatus can include a water reservoir connected to the water outlet, first and second water reservoir water level detectors for detecting high and low water levels in the water reservoir, and a flow control for controlling flow of water from the water outlet of the container into the water reservoir. The slow sand filter apparatus can include a raw water reservoir connected to the water inlet of the apparatus and a control for controlling flow of water from the raw water reservoir to the sand filter apparatus.

The slow sand filter apparatus can include a mechanism which can enable a top surface of the filter material to be cleaned. The cleaning mechanism can be a manually operatable mechanical agitator. The mechanical agitator can comprise an agitator blade, which can contact the top surface of the filter material, and a rotatable shaft and handle which can enable the agitator to be manually rotated. The agitator blade can include any one of a scraper blade, scraper teeth, scraper paddles, scraper forks, L-shaped scrapers and T-shaped scrapers. The mechanical agitator can be journalled for rotation in a water diffuser which can be located in the upper portion of the container.

The invention is also directed to a method of operating a slow sand filter, the filter including a container, filter material partially filling the container, a water inlet above the filter material and a water outlet within the filter material, the method comprising the steps of: maintaining water level in the container above the top of the filter material at a level which is a balance between (1) a water maintenance level that is sufficiently deep that water falling from the water inlet onto the top of the water in the container does not significantly disturb the schmutzdeuke layer; and (2) a water maintenance level that is sufficiently shallow that oxygen from the air above the water level can diffuse through the water and reach the schmutzdeuke layer so that the schmutzdeuke layer is maintained in living condition even when there is no flow of water through the water inlet.

BRIEF DESCRIPTION OF DRAWINGS

In drawings which illustrate specific embodiments of the invention, but which should not be construed as restricting the spirit or scope of the invention in any way.

DETAILED DESCRIPTION OF SPECIFIC EMBODIMENTS OF THE INVENTION

It is common knowledge among environmental engineers that slow sand filters, which are not designed for intermittent operation, fail to perform satisfactorily when intermittently operated (see *Slow Sand Filtration for Community Water Supply,* Visscher, Paramasivan, Raman and Heinjnen, Technical Paper Series No. 24, International Reference Centre for Community Water Supply and Sanitation, The Hague, Netherlands; also, *Slow Sand Filtration,* a report prepared by the Task Committee on Slow Sand Filtration of the Environmental Engineering Division of the American Society of Civil Engineers, 1991). The decline in performance of the slow sand filters is reported to coincide with the decline in dissolved oxygen levels in the water above the sand surface (see *Effect of Intermittent Operation of Slow Sand Filters on Filtered Water Quality,* Paramasivan, Joshi, Dhage and Taijne, 1980, Indian Journal of Environmental Health, Vol. 22, No. 2, p. 136–150). These results were obtained by observing full scale continuously operated slow sand filters which treated natural water supplies.

The inventor has discovered that by maintaining the static water level above the top of the sand (or other filter material)

(1) above a minimum depth, such that the bio-organic water treatment layer (called the schmutzdeuke) does not dry out or become disturbed by the incoming water supply, thereby perforating the schmutzdeuke layer and permitting raw untreated water to penetrate through the schmutzdeuke layer; and (2) below a maximum depth, such that oxygen from the air can reach the schmutzdeuke layer and thus the schmutzdeuke is not killed by oxygen deficient stagnant water, the schmutzdeuke can be preserved in living form, even under intermittent operating conditions, and the effectiveness of the slow sand filter can be maintained, even when the supply of water is intermittent. The static water level, or maintenance water level, is defined as the water level in the slow sand filter while it is not being operated, that is, not being used to supply water.

The schmutzdeuke layer of the intermittently operating slow sand filter of the present invention will typically survive for at least one weekend and may survive for at least a week in conditions of no flow of water from one period of flow of water through the filter to the next. Such conditions can occur while a cottager is away from a country cottage. Ultimately, in cases where there is a prolonged period of no water flow, the schmutzdeuke is not killed off by a lack of oxygen but by a lack of food. By providing a life for the schmutzdeuke greater than 48 hours during periods when there is no flow of water through the slow sand filter, the present invention is a significant advance over the prior art.

This is a surprising discovery because it was previously considered in the art that the schmutzdeuke dies quickly in slow sand filters in which the water has not been flowing.

Normal continuous operation of a slow sand filter results in the biological layer (schmutzdeuke) increasing in thickness over time. This results in a consequent reduction of flow of water. In continuous systems, it is therefore necessary from time to time to shut down the slow sand filter and physically reduce the thickness of the schmutzdeuke layer by scraping away some of the layer. Intermittent operation of the slow sand filter of the present invention therefore provides secondary benefit because it actually improves water flow due to the slight starvation and size reduction of the biological layer (schmutzdeuke).

One embodiment of the intermittently operating slow sand filter uses the damming of water in a raised pipe to provide a constant maintenance level of water in a slow sand filter container. The container includes a water inlet and outlet, and is partially filled with sand or other filter material. A pipe from the water outlet in the slow sand filter is raised upward to the desired level of water over the sand before descending to a water reservoir. Water backs up in the pipe and the container to the desired water level above the top of the sand, even when the flow of water is intermittent. The schmutzdeuke automatically and naturally forms at the top of the filter medium. Preferably, the water level in such a manually operated slow sand filter, using fine quartz sand as the filter medium, and at ambient temperatures (about 21° C.) is maintained above about 1 cm above the top of the filter medium and below about 8 cm above the top of the slow sand filter.

In another embodiment of the intermittently operating slow sand filter, according to the invention, the water level is maintained automatically, when not being used, at a desired minimum maintenance level, and otherwise is kept within a desired range of levels above the top of the sand (or other filter material) in a partially filled container.

Automatic control is provided by a system that senses the minimum and maximum water level in the slow sand filter. The supply of water may be from a pump or from a gravity flow controlled by a valve. During times when water is not being taken from the slow sand filter, the water level is maintained at a desired maintenance level, within a range such as specified above for the manually operated slow sand filter.

The water from an automatic intermittently operating slow sand filter is preferably supplied to a reservoir. Water level in the reservoir may also be controlled within a desired range using a combination of upper and lower level limit detectors and a valve on an outlet line from the container to the reservoir.

The design and operation of the intermittently operated slow sand filters according to the invention have been carefully developed to eliminate the problems associated with continuously operated slow sand filters when stopped. The intermittently operated slow sand filter has also been extensively tested in both field and laboratory conditions using natural water supplied (see M. Eng. Thesis by B. Buzunis, entitled *Intermittently Operated Slow Sand Filtration: A New Water Treatment Process,* University of Calgary, 1995). A pilot study of an intermittently operated slow sand filter using natural water supplies has indicated that the dissolved oxygen concentration at the surface of the sand could be maintained at a sufficiently high level that the performance of the slow sand filter was never impaired, even though the filter was intermittently operated. In comparison, the work by Paramasivan, et al., reported above, reports failure of large scale continuously operated slow sand filters when their operations were stopped for similar periods of time.

The rate with which dissolved oxygen is consumed by the living schmutzdeuke at the sand surface is a function of the magnitude of the accumulation of microorganisms, organic material and inorganic material (collectively known as the biological layer or schmutzdeuke), at the sand surface and is not a function of how this accumulation is achieved (that is, the manner with which the filter is operated, continuously or intermittently). It follows that a continuously operated filter with a large depth of water over the sand, when it is stopped, exhibits similar dissolved oxygen consumption to an intermittently operated filter with the same depth of water, when it is paused or interrupted, provided both types of filters have similar biological layers and the duration of the stop and/or pause is similar. Therefore, results from a completely stopped continuously operated filter and a paused intermittently operated filter would be comparable. It follows that the work of Paramasivan et al. on the continuously operated slow sand filter would apply to the intermittently operated slow sand filter.

Figures 1, 2:
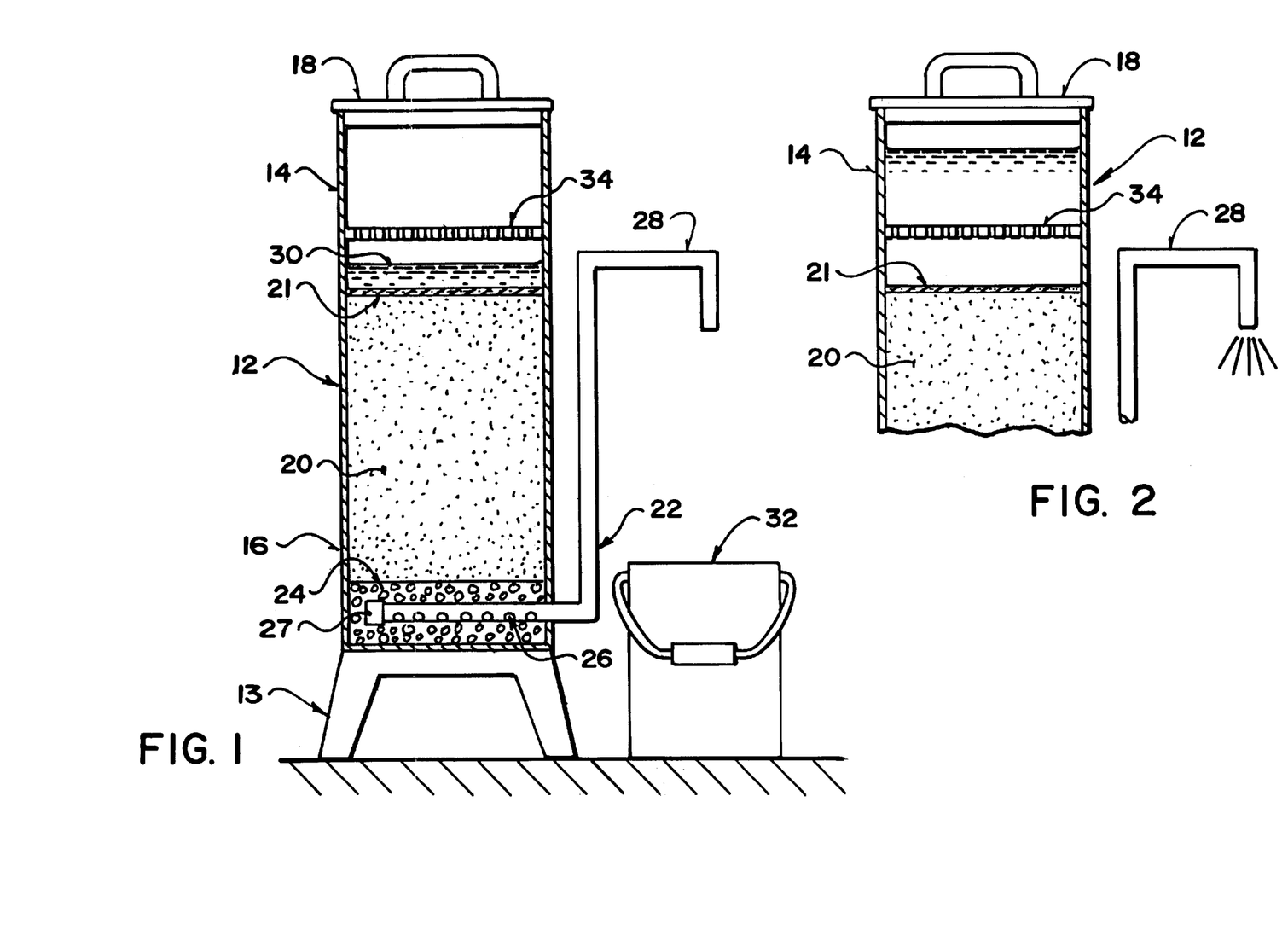
FIG. 1 is an elevation section view of a manually operated intermittently operating slow sand filter, according to the invention, in resting condition.
FIG. 2 is an elevation section view of the top portion of the apparatus shown in FIG. 1 in operating condition.

Referring to FIGS. 1 and 2, there is shown a manually operated slow sand filter, according to the invention, for use with an intermittent supply of water. The unit is intended, for example, for stand alone intermittent use in a person's dwelling. The slow sand filter includes a watertight container 12 having an upper portion 14 and a lower portion 16. The container 12 is supported on a base or support stand 13. The container 12 is preferably about 1 m to 1.2 m high and of variable cross-section, though for household use it may have a diameter of about 40 cm. The container 12 may be made of plastic such as PVC, or of concrete or other material suitable for containing potable water. The upper portion 14 of the container 12 is covered by a cover 18, which preferably should completely cover the open top of the container 12 to prevent dust and other debris from entering the container 12.

The open top of the container 12 forms a water inlet, which allows water to be poured into the open top of the container 12. The lower portion 16 of the container 12 is filled to a depth of 40 cm or more with fine washed quartz sand 20, or other filter material suitable for use with slow sand filters (as, for example, described in U.S. Pat. No. 5,032,261, Piper). A water outlet 22 is formed in the base of the lower portion 16 of the container 12. The lower end of the water outlet 22 includes an underdrain layer of gravel 24 which underlies the sand 20, and a perforated drain pipe 26 lying within the gravel 24 and extending out through a hole in the lower portion 16 of the container 12 and terminating at its upper end as a spout 28. The drain pipe 26 is a perforated PVC pipe of about 12 mm diameter, as are all the pipes described herein, with 3 mm diameter holes spaced 25 mm between centers along the bottom of the perforated pipe 26. The drain pipe 26 in the sand 24 is sealed at one end with a 12 mm PVC cap 27. The gravel 24 is preferably washed 19 mm quartz gravel, or the like. The perforated end of the pipe 26 is embedded in the gravel 24 with a depth of about 5 cm of gravel above the crown of the perforated pipe 26.

The level 30 of the water in the container 12 must be maintained between minimum and maximum levels above the top 21 of the sand 20, preferably in the range 1 cm to 8 cm above the top of the sand 20. This is done by appropriate markings on the container 12. The water in the container is at ambient temperature (that is, not heated), as for example, 21° C., and at ambient pressure (atmospheric pressure). The lower water level, that is, 1 cm, is selected to be sufficiently deep to prevent drying of the schmutzdeuke layer 21, which will kill the schmutzdeuke, or cause disturbance of the schmutzdeuke layer 21 due to turbulence from water falling onto the top of the water 30 standing in the container 12.

The upper water level 30 is selected so that it is shallow enough to prevent stagnation, that is, loss of transport of oxygen from the air above the surface of the water 30 to the schmutzdeuke layer 21 during periods when there is no fresh raw water supply. The term "stagnation" is used herein to define the condition in which the water above the schmutzdeuke 21 at the top of the sand 20 is so deep that it becomes deprived of oxygen and the schmutzdeuke dies. The schmutzdeuke layer 21 uses up oxygen in the water and if the water above the schmutzdeuke 21 is so deep that air above the water 30 cannot reach the schmutzdeuke layer 21, the layer 21 will die. The actual upper water level 30 is believed to depend in part on the type of filter medium, and the ambient temperature, and is readily experimentally determinable. The range of 1 cm to 8 cm is known by the inventor to be beneficial for fine quartz sand at 21° C. In general, the lower the maximum water level 30 (but higher than 1 cm), the better. Hence a water fluctuation range 1 cm to 5 cm is preferred.

The water level may be maintained by extending the pipe 26 out from the water outlet upward to the desired level as indicated at spout 28. The water level so maintained is indicated at 30. This water level 30 is maintained at a minimum level even when the sand filter is not being operated, that is, when the filter is not been replenished with raw water. This is known as a resting condition. FIG. 2 illustrates a section elevation view of the upper portion 14 of the filter 12 in initial operating condition. During operation, when raw water is first introduced, the water level will initially rise, as indicated in FIG. 2, and gradually reduce to the desired level 30 shown in FIG. 1 as the filtered water drains down through the sand 20, the gravel 24 and into the perforations of the pipe 26. Filtered water can be collected in a bucket or other suitable potable water reservoir 32, or pumped to a portable water reservoir as shown in later drawings. Under such conditions, a schmutzdeuke naturally forms in the top layer 21 of the sand.

Figure 5:
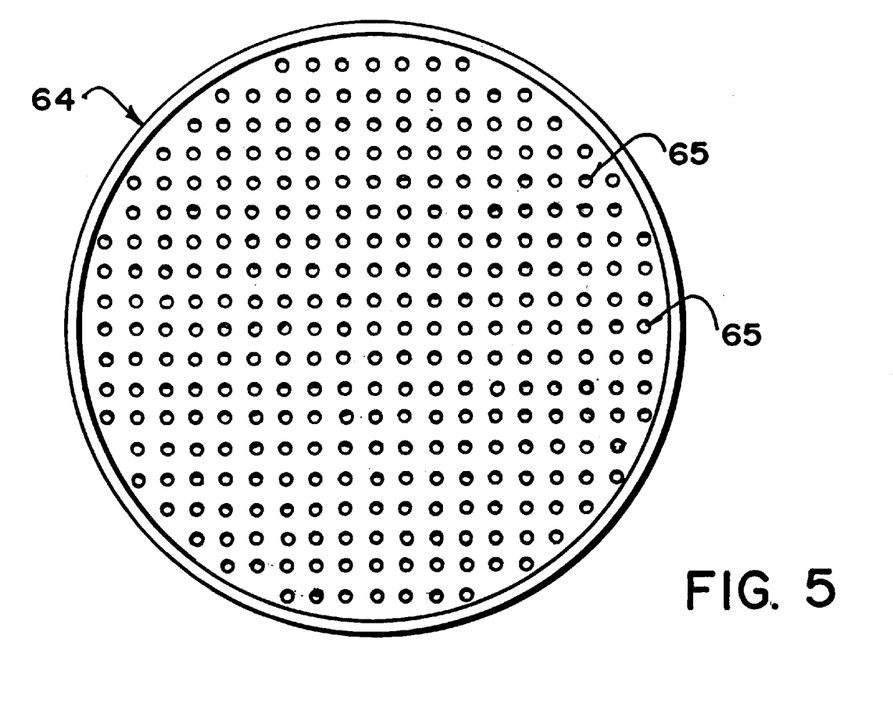
FIG. 5 is a plan view of a diffuser plate for use in the apparatus of FIG. 3.
Figure 6:
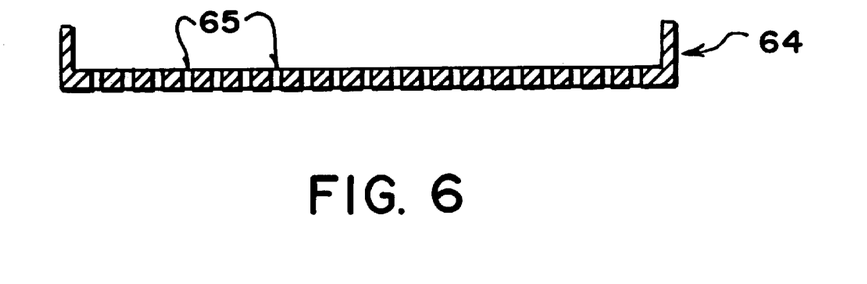
FIG. 6 is a side section view of the diffuser plate of FIG. 5.

When water is added to the top of the container 12 during operation, it may disturb the delicate schmutzdeuke layer 21 unless it is added carefully. To prevent disturbance of the sensitive schmutzdeuke layer 21, it is preferable to include a diffuser 34 secured by any suitable means such as that shown in FIG. 4 to the walls of the container 12 above the schmutzdeuke layer 21 of the sand 20. The diffuser 34 must be capable of diffusing the raw water evenly and distributing the raw water at a rate greater than the rate of raw water supplied to the filter. The diffuser 34 is shown in more detail in FIGS. 5 and 6, and is perforated with 2 mm holes spaced about 1 cm apart and located about 10 cm above the schmutzdeuke layer 21 of sand 20, and at least higher than the desired water level 30 shown in FIG. 1. Water entering the container 12 during operation initially accumulates above the diffuser 34 and gradually percolates onto the schmutzdeuke layer 21 without disturbing it.

In operation, the container 12 will normally be filled with water to the desired level 30 between a maximum and minimum and the schmutzdeuke layer 21 is alive. To operate the filter in its simplest form, the cover 18 is removed and raw water is poured into the top of the container 12. Filtered water will subsequently begin flowing into the potable water reservoir 32. The filtered water will continue to drain from the filter until the level of the water 30 above the schmutzdeuke layer 21 is below the bottom of the drain pipe spout 28. In operation, the thickness of the living schmutzdeuke layer 21 increases over time. Maintenance is required when the thickness of the schmutzdeuke layer 21 develops to a point where it reduces the flow rate of water through the filter to below acceptable levels. Maintenance typically consists of removing the schmutzdeuke layer 21 and 1 or 2 cm of sand along with it. The manually operated filter can be expected to be back in operation one day after being cleaned.

Figure 3:
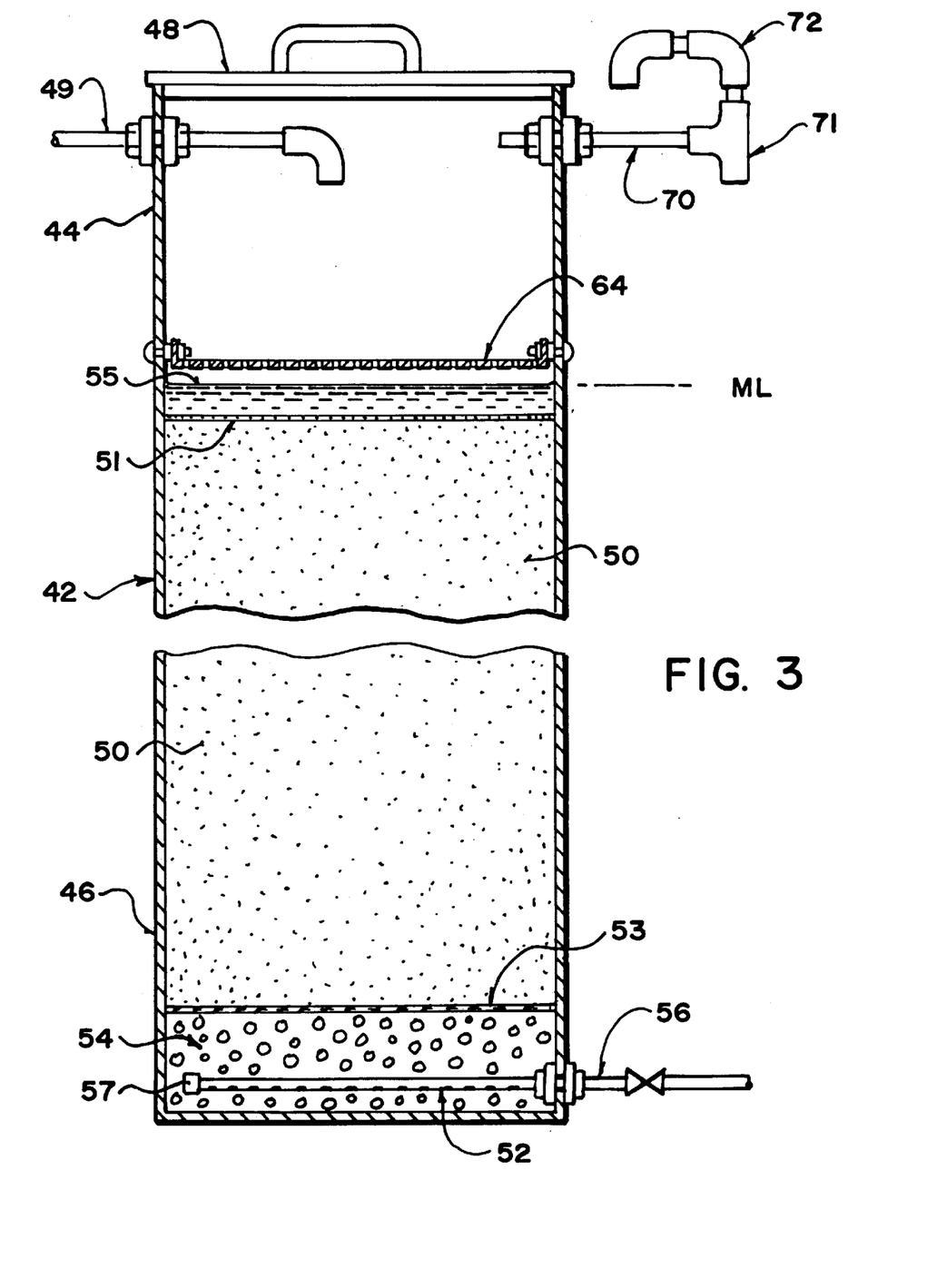
FIG. 3 is an elevation section view of an automatically operated intermittently operating slow sand filter according to the invention.

An automatically operated slow sand filter for use with an intermittent supply of raw water is illustrated in FIGS. 3 to 8. The automatic unit is intended, for example, for providing a continuously available and often intermittent supply of filtered potable water to household faucets without householder participation. The automatic slow sand filter as illustrated in FIG. 3 includes a watertight cylindrical container 42 having an upper portion 44 and a lower portion 46 of similar construction and size to the container 12, shown in FIG. 1, and having a similar cover 48. A raw water inlet pipe 49 passes through the wall of an upper portion 44 of the container 42 and forms a downwardly facing raw water intake. The lower portion 46 of the container 42 is filled to a depth of 40 cm or more (for example, 61 cm) with filter material 50 such as quartz sand, similar to the filter material 20 shown in FIG. 1.

A water outlet layer 52 is formed in the lower portion 46 of the container 42. The water outlet layer 52 at the base of the container 42 includes an underdrain layer of gravel 54 underlying the filter sand 50 above it, and a perforated pipe 56 associated with the gravel 54. The pipe 56 has an end cap 57. The pipe 56 lies within the gravel 54 and extends out through a hole in the lower portion 46 of the container 42. The gravel 54 and sand 50 are preferably separated by a geomembrane 53. Pipe 56 leads to a potable water reservoir 62 (shown in FIGS. 7 and 8). Preferably, the pipe 56 is embedded in at least 20 cm of gravel 54. The rate of flow through the raw water intake 49 must be greater than the maximum rate of flow through the filter sand 50 to maintain a water level above the top of the sand 51 and thereby maintain the schmutzdeuke layer 51 in living condition.

The water level 55 should be between 1 cm and 8 cm above the schmutzdeuke layer 51 and preferably between 1 cm and 5 cm. Sensors positioned at the 1 cm and 5 cm levels can be used to ensure the water level 55 stays within those limits.

Figure 4:
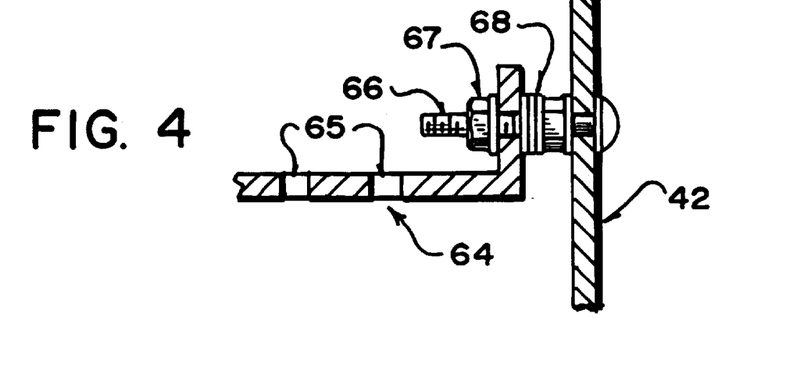
FIG. 4 is a detail of a diffuser plate holder for use in the apparatus of FIG. 3.

When raw water is added to the container 42 through inlet 49 during operation, it may disturb or perforate the schmutzdeuke layer 51 unless the water is added carefully. To prevent turbulent disturbance of the schmutzdeuke layer 51 and ensure that all the raw water is forced to pass through the schmutzdeuke layer 51 and not bypass it, it is preferable to include a diffuser 64, shown particularly in FIGS. 5 and 6. The diffuser 64 is perforated in the same manner as the diffuser 34 of FIG. 1, with evenly distributed holes 65. The diffuser 64 is secured to the container 42 as shown in FIG. 4 with a bolt 66, a nut 67 and washers 68 to the container 42 above the schmutzdeuke layer 51 of the sand 50 and the water level 55. Preferably, the diffuser 64 is located about 8 cm above the layer 51 of the sand 50, and 5 mm above the minimum water level 55 (also referred to as the maintenance water level ML) and must be capable of distributing water at a rate greater than the raw water supplied to the filter container 42 through inlet pipe 49. Raw water entering the container 42 during operation passes through the holes 65 in the diffuser 64 onto the top of water level 55 and gradually percolates downwardly onto the schmutzdeuke layer 51 of sand without disturbing it, or causing undesirable holes therethrough.

In the upper portion 44 of the container 42, there is an escape pipe 70 which extends through the wall of the container 42 and is fitted with a drain 71 and air vent 72. Pipe 70 is at the same level as pipe 49. Pipe 70 with drain 71 acts as an emergency drain and must have the same water passing capacity as the inlet pipe 49. The air vent 72 allows air to escape from within the container 42 and must be of sufficient capacity to allow air in the top of the filter to escape while the container 42 is being filled with raw water, and alternatively to enter the top of the filter when water is being drained from the filter. Air in the upper portion 44 of the filter should be at atmospheric pressure.

Figure 7:
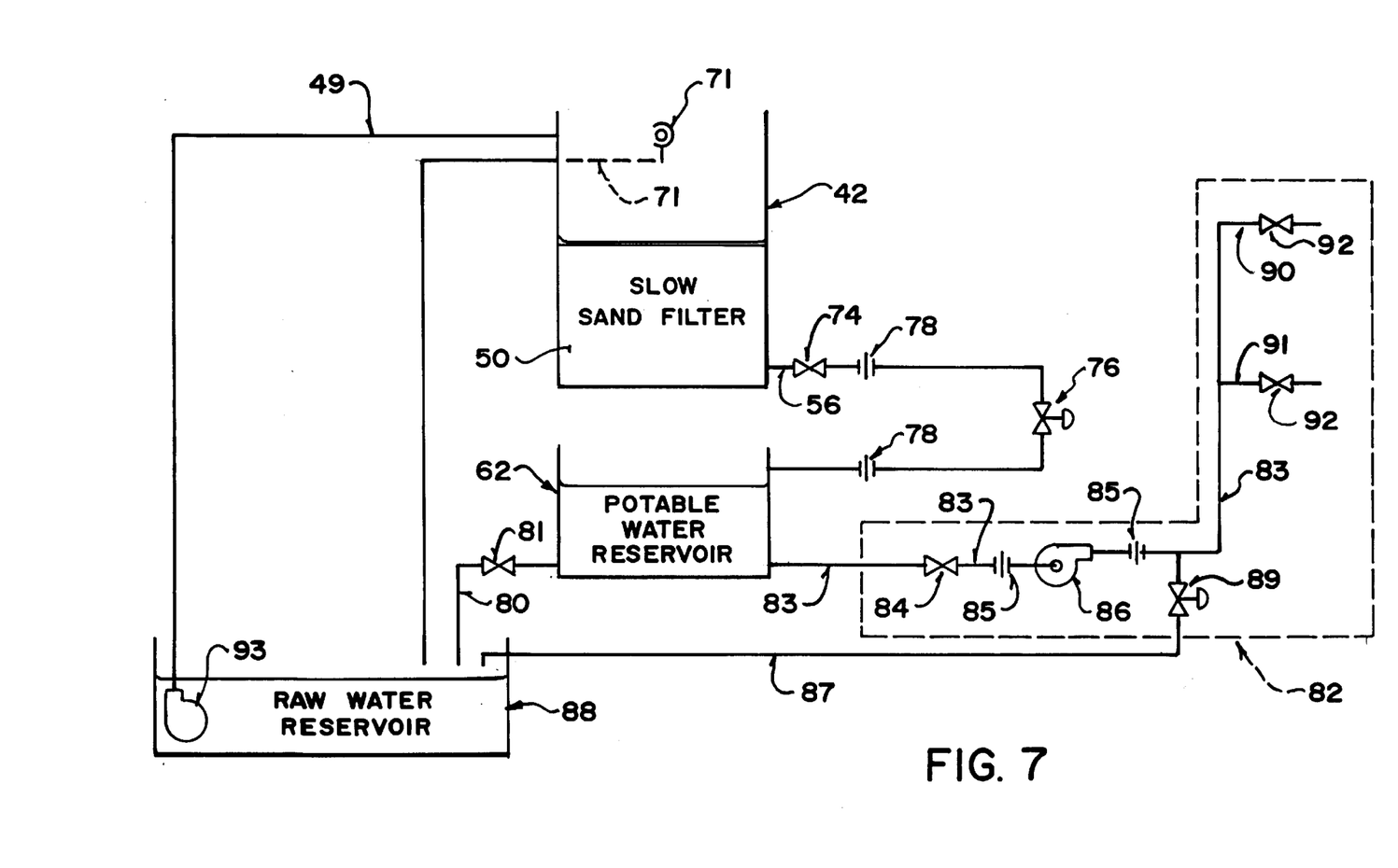
FIG. 7 is a fluid flow schematic of the apparatus shown in FIG. 3 in combination with a raw water reservoir and a potable water reservoir.
Figure 8:
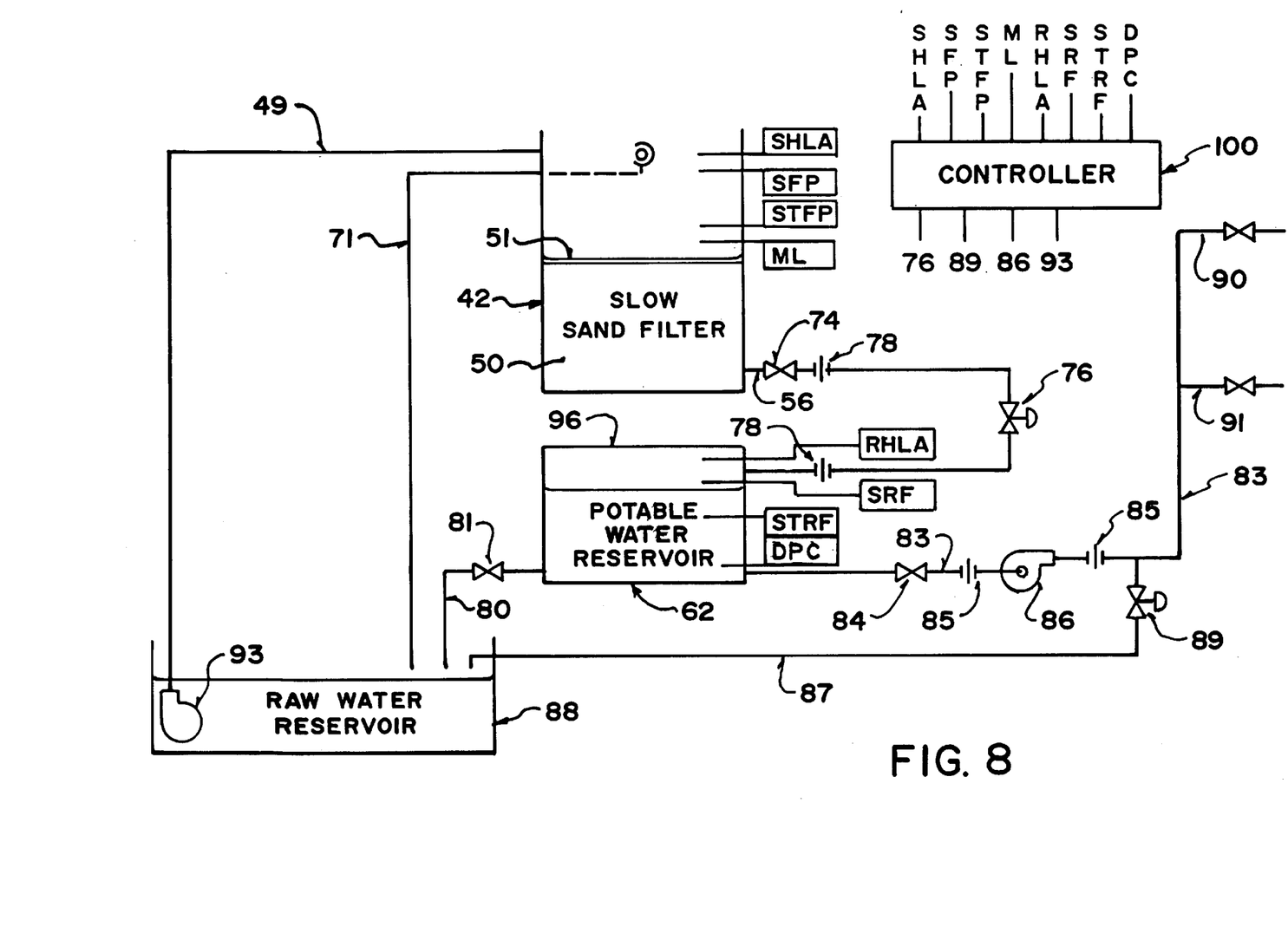
FIG. 8 is a control system schematic for use with the apparatus shown in FIG. 3 in combination with a raw water reservoir and a potable water reservoir.

Referring now to FIGS. 7 and 8, which illustrate respectively, fluid flow and control system schematics, rate of water flow from the slow sand filter container 42 to potable water reservoir 62 through pipe 56 is controlled by a suitable means such as a ball check valve 74 and a solenoid valve 76. Pipe 56 is formed by three lengths of 12 mm PVC tubing joined at unions 78, and the solenoid valve 76 is located on the central section of the tubing. The final section of tubing 56 leads into the potable water reservoir 62. The potable water reservoir 62 is sized to contain a water supply sufficient for normal use. Flow from the potable water reservoir 62 may be conducted via drain line 80 through ball check valve 81, or by the water distribution system 82 (shown in dotted border) on outlet line 83. The distribution system 82 is isolated from the potable water reservoir 62 by a ball check valve 84 on line 83, and provides potable water for use by the consumer as required, or return of the water to the raw water reservoir 88. Distribution of the water in line 83 is driven by pump 86 secured in line 83 between two unions 85. Water from the pump 86 may be returned to the raw water reservoir 88 along line 87 under control of solenoid valve 89 on line 87, when clean water is required to freshen the filter 42, or along a continuation of line 83 to lines 90 and 91 where potable water may be made available from hand operated valves (such as faucets) 92 typically installed in the home.

Water is supplied from the raw water reservoir 88 to the sand filter container 42 using pump 93 on intake line 49. If the raw water reservoir 88 is elevated above the container 42, gravity applies and the feed pump 88 may be replaced by a solenoid valve. The feed pump 88, or solenoid valve, constitute a water inlet control means for controllably supplying water to the raw water inlet line 49. The drain 71 (see also FIG. 3) may be returned directly to the raw water reservoir 88 or to waste.

Control of water levels in the container 42 and in the potable water reservoir 62 is accomplished using the water flow controls just described and water level detectors in the container 42 and potable water reservoir 62. As seen in FIG. 8, the water level detectors in the container 42 detect the following water levels: (1) a maintenance level 55 (ML) (see FIG. 3), 25 mm above the schmutzdeuke layer 51 of the sand 50 (see also FIG. 3); (2) a high level alarm (SHLA), located 18 cm above the layer 51 at the top of the sand 50 (to prevent overflow); (3) a stop feed pump (SFP), located 15 cm above the layer 51; and (4) a start feed pump (STFP), located 50 mm above the layer 51 of the sand 50. These levels and the foregoing acronyms are shown in FIG. 8. To maintain the schmutzdeuke in living condition, even when there is no water flow, the water level 55 must be maintained during periods of nonuse within acceptable distance of the maintenance level ML. The maintenance level ML is selected according to the schmutzdeuke maintaining criteria described above for the manually operated slow sand filter. As a general rule, the water level 30 (see FIG. 1) or water level 55 (see FIG. 3) should be at a depth of between 1 cm and 8 cm above the top of the sand 20 or 50, and preferably between 1 cm and 5 cm.

As seen in FIG. 8, water levels in the potable water reservoir 62 are detected by detectors that detect the following levels: (1) a high level alarm (RHLA), 2.5 cm from the top 96 of the reservoir 62; (2) a stop reservoir flow (SRF), 7.5 cm from the top 96 of the reservoir 62; (3) a start reservoir flow (STRF), 20.0 cm from the top 96 of the reservoir 62; and (4) distribution pump cutoff (DPC), 5.0 cm from the bottom 98 of the reservoir 62, above the outlet lines 80 and 83. The detectors with the foregoing acronyms are shown schematically at the appropriate levels in FIG. 8.

When potable water is used from lines 90 or 91, usually through faucets 92 (see FIG. 7), water must be pumped from the potable water reservoir 62 and this water must be replaced. The following description therefore describes the water fill cycle for the potable water reservoir 62. When water is required from the lines 90 and 91, the distribution pump 86 is automatically turned on, thereby forcing potable water from the reservoir 62 along line 83 to one of lines 90 and 91 (there may be other lines similar to 90 and 91 as required). The water level in the potable water reservoir 62 thus drops. When the water in the potable water reservoir 62 drops to the level detected by detector STRF, solenoid valve 89 is turned on and the raw water feed pump 93 is started. The feed pump 93 supplies raw water to the slow filter container 42 faster than it can be drained out through outlet line 56, thereby causing the water level 55 (see FIG. 3) in the container 42 to rise. When the water level in container 42 rises to and is detected by detector SFP, the feed pump 93 is turned off, thereby stopping the flow of water through line 49 into the container 42. Water in the container 42 will continue to percolate downwardly through the sand 50 and flow into the pipe 56 and subsequently into the potable water reservoir 62 until the STFP detector level is reached in the container 42. Then the feed pump 93 is turned on again. This cycle is then repeated as required to fill the potable water reservoir 62.

When the water in the potable water reservoir 62 reaches the level detected by SRF due to supply of water from container 62 through line 56 from container 42, the feed pump 93 is stopped but solenoid valve 76 stays open. This allows further potable water to drain from container 42 through line 56.

It is desirable to drain the container 42 to the maintenance level ML (preferably between 1 cm and 5 cm above the schmutzdeuke layer) during times when the potable water supply from reservoir 62 is not being used, since this is the optimum level for maintaining the schmutzdeuke in living condition. The following procedure, which forms part of the potable water reservoir fill cycle, accomplishes this. The water level in the potable water reservoir 62 is allowed to rise to the level detected by RHLA through draining of filtered water from the container 42 via line 56 and when this level is reached, solenoid valve 89 is opened to drain the potable water reservoir 62 into raw water reservoir 88. When the water level in the potable water reservoir 62 drops to the level detected by SRF, solenoid valve 89 closes. Filtered water then continues to drain through line 56 from the container 42 into reservoir 62 and these steps are repeated as required until the water level in the container 42 reaches ML, at which point the solenoid valve 76 is closed. This concludes the potable water reservoir 62 fill cycle. The process is repeated as required.

When water is not used from the potable water reservoir 62 for 24 hours, it is desirable to refresh the water in the potable water reservoir 62 (termed refresh cycle). Solenoid valve 89 is opened, thereby allowing potable water from reservoir 62 to drain into the raw water reservoir 88 until the level of water in the potable water reservoir 62 drops to the level detected by STRF, at which point valve 89 is closed. Fresh potable water then drains through line 56 into reservoir 62.

If water in the container 42 rises to the level detected by SHLA, the water level is too high in the container 42, and it must be lowered using the following potable water reservoir high level reduction cycle. The raw water feed pump 93 is turned off until the water level in the container 42 drops to level ML and valve 89 is opened until the water level in the potable water reservoir 62 lowers to the level detected by STRF. The level of the water in the container 42 will then be at ML and the potable water reservoir 62 fill cycle may then be started by activating valve 76.

If the water level in the potable water reservoir 62 drops to the level detected by DPC, the water level in the potable water reservoir 62 must be raised. This is done simply by turning off the distribution pump 86 to lines 90 and 91 until the water level in the potable water reservoir 62 rises to the level detected by STRF.

The algorithms for the procedures described above are programmed into a microcontroller 100 which is connected to receive signals from each of the detectors SHLA, SFP, STFP, ML, RHLA, SRF, STRF and DPC (see FIG. 8), and to control the pumps 86 and 93 and each of the solenoid valves 76 and 89. The controller 100 may be a programmable logic controller (PLC) such as model No. 1747-L20C/F 12-DC SNK 8-RLY available from Allen Bradley Co., programmed according to the software attached hereto as Schedule A. Alternatively, it may be a CPU (for example, Microchip PIC16C55/57 VLSI controllers) programmed in similar manner. The software carries out the process control steps described herein and can be readily programmed by any skilled programmer from the description in this specification. The controller 100 provides signals to the pumps 86 and 93 and valves 76 and 89 to control their operation and maintain the water levels at desired levels.

Figures 9, 10:
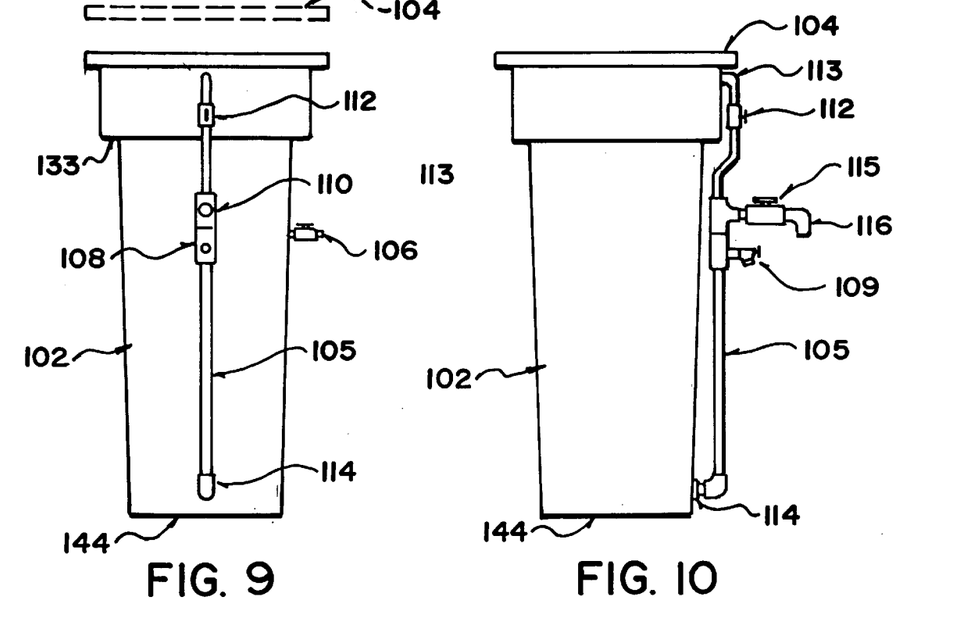
FIG. 9 is an elevation of a second embodiment of automatic intermittently operating slow sand filter according to the invention.
FIG. 10 is a side view of the automatic intermittently operating slow sand filter shown in FIG. 9.

We now go on to describe a second embodiment of the invention as illustrated in FIGS. 9 through 22. FIG. 9 is an elevation of a second embodiment of automatic intermittently operating slow sand filter according to the invention, including a clean-in-place feature. As seen in FIG. 9, the slow sand filter is constructed of a downwardly tapering container 102 with a cover 104 at the top thereof. The downwardly tapered shape is useful for shipping purposes because a number of containers can be stacked together to conserve space. A shelf 133 is formed in the circumference of the top portion of the container 102. Fitted on the exterior of the container 102 is a vertical pipe 105. The vertical pipe 105 has therein a drainage valve 106, a maintenance valve location 108, a filter outlet 110, an anti-siphoning valve 112 and a bulkhead connector 114 at the bottom region thereof, above the base 144. The utility of these fittings will be explained below.

FIG. 10 is a side view of the second embodiment of the automatic sand filter, as illustrated previously in FIG. 9. The vertical pipe 105 is connected at the bottom of the container 102 via bulkhead connector 114. A maintenance valve 109 is connected at the maintenance valve location 108 (see FIG. 9). The pipe 105 also has connected therein a treated water spout 116 with a calibration valve 115 on the top of the valve. The top of the pipe 105 is connected to the top portion of the connector 102 via anti-siphoning hole 113.

Figure 11:
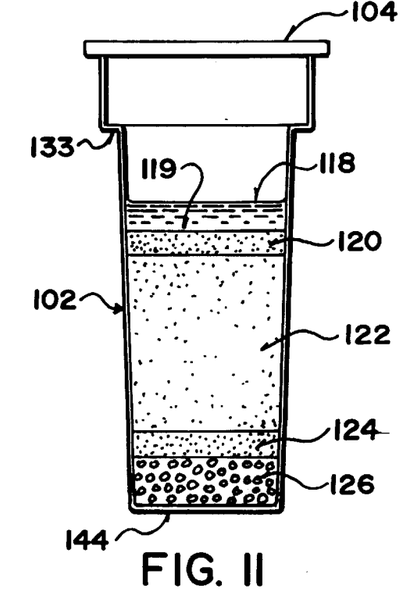
FIG. 11 is a front section view of the automatic intermittently operating slow sand filter shown in FIG. 9.

FIG. 11 illustrates a front section view of the second embodiment of the intermittently operating slow sand filter as shown previously in FIGS. 9 and 10. The interior of the container 102 has disposed therein in stacked configuration a layer of top sand 120, an underlying second layer of sand 122, an underlying third layer of sand 124, and a bottom layer of gravel 126. The grades and screen sizes of sand making up the top sand layer 120, the second sand layer 122, and the third sand layer 124 can be varied in quality and diameter in order to provide desired filter flow rates and characteristics for the second embodiment of the automatic intermittently operating slow sand filter. The standing water level 118, as explained previously is set so that it provides a balance between being shallow enough to enable oxygen from the top surface of the water level 118 to permeate downwardly to the schmutzdeuke layer 119 at the top of sand layer 120, while at the same time, being deep enough that water turbulence caused by fresh raw water being admitted into the top of the container 102 will not disturb or perforate the schmutzdeuke layer. For the most satisfactory operation, the water level 118 should be between about 1 cm and 8 cm above the top of the top sand layer 120, with a range of 1 cm to 5 cm being preferred.

Figure 12:
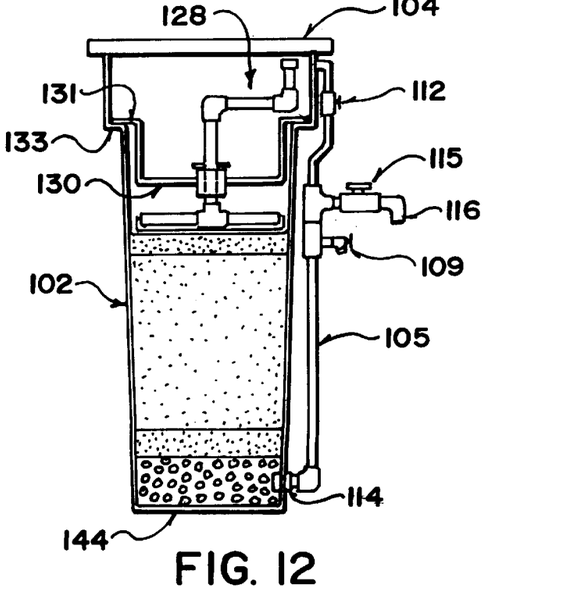
FIG. 12 is a side section view of the automatic intermittently operating slow sand filter shown in FIG. 10 with clean in place apparatus.

FIG. 12 illustrates a side section view of the second embodiment of the automatic intermittently operating slow sand filter with a clean in place apparatus. As seen in FIG. 12, the container 102 contains in the top region thereof above the top of sand layer 120 a hand operatable mechanical agitator 128 penetrating through the centre of a diffuser basin 130. The rim of the diffuser basin 130 rests on shelf 133, which is formed around the circumference at the top region of the container 102. The vertical pipe 105, as discussed previously in association with FIGS. 9 and 10, is connected at the bottom of the container 102 via bulkhead connector 114. The pipe 105 has fitted therein a maintenance valve 109, a treated water spout 116, a calibration valve 115, and an anti-siphoning valve 112 as described previously. The anti-siphoning valve 112 is important because it prevents raw water from being siphoned from the top region of the container 102 and into the treated potable water spout 116.

Figure 13:
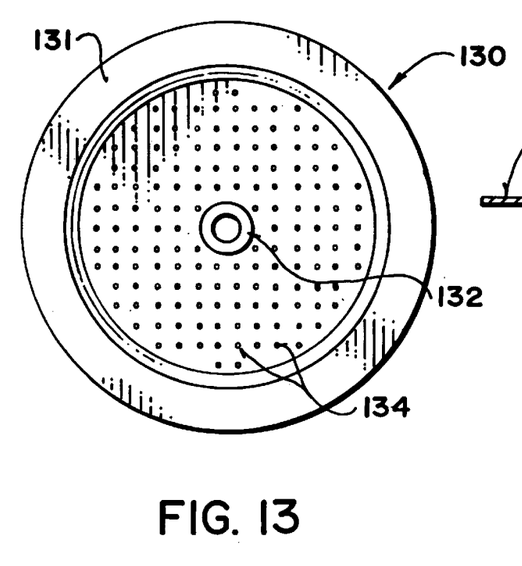
FIG. 13 is a plan view of a diffuser for use in the apparatus of FIG. 12.

FIG. 13 illustrates a plan view of a diffuser basin 130. The diffuser basin 130 has around the periphery thereof a basin rim 131, which is adapted to rest on circumferential shelf 133 of container 102, as seen in FIG. 12. The diffuser basin 130 has a series of perforations 134 (drainage holes) formed in a grid-like pattern in the bottom of the diffuser basin 130. The size and number of the perforations 134 in the bottom of the basin 130 are designed to ensure that negligible turbulence is created in the water 118 below the basin 130 (see FIG. 11) and at the same time permit adequate water flow rate so that there is no back-up.

Figure 14:
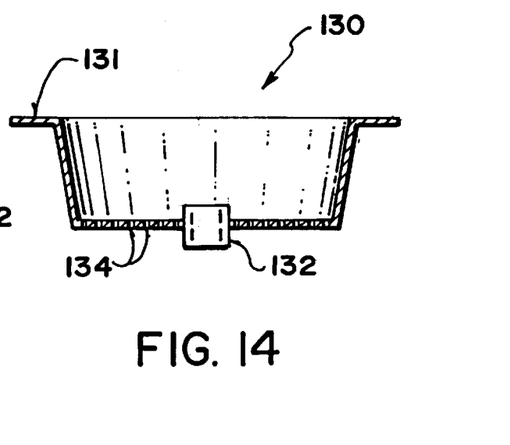
FIG. 14 is a side section view of the diffuser of FIG. 13.

A mechanical agitator bulkhead 132 is located in the centre of the base of the diffuser basin 130. The bulkhead 132 is designed to admit the vertical stem of the mechanical agitator 128, and allow the mechanical agitator 128 to rotate relative to diffuser basin 130. FIG. 14 illustrates a side section view of the diffuser basin of FIG. 113. The basin rim 131 around the top circumference and the mechanical agitator bulkhead 132 in the centre of the bottom are shown.

Figure 15:
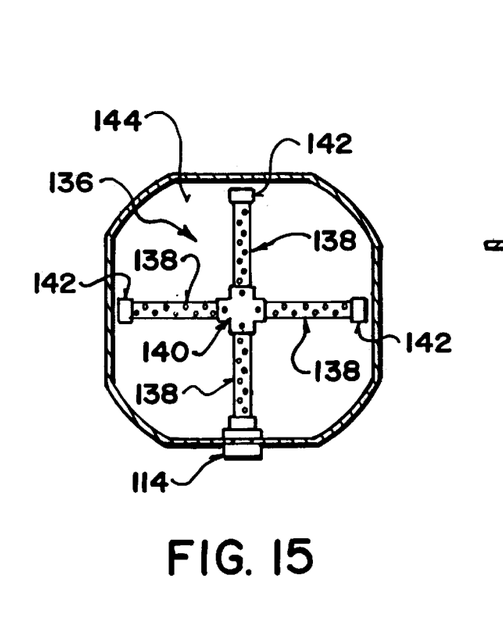
FIG. 15 is a top view of an underdrain assembly for use in the bottom of the apparatus of FIG. 12.

FIG. 15 is a top view of an underdrain assembly for use in the bottom layer of gravel 126 of the apparatus illustrated in FIG. 11.

The underdrain assembly 136 is constructed of a central cross-shaped pipe connector 140, which has connected thereto at 90° positions four radially extending perforated pipes 138. Three of the perforated pipes 138 have caps 142 at the free ends thereof. The free end of the fourth perforated pipe 138 (the bottom pipe as seen in FIG. 15) connects to the bulkhead connector 114, which can be seen in FIGS. 9, 10 and 12. The underdrain assembly 136 is immersed in the gravel layer 126 (see FIG. 11) a short distance above the base 144 of the container 102. The underdrain assembly 136 enables filtered water that has percolated downwardly through the overlying layers of sand 120, 122 and 124 to collect in the underdrain assembly 136 and be pumped out through bulkhead connector 114. The size and number of perforations in the pipes 138 are designed to ensure that filtered water can readily enter the assembly 136 and be exhausted through connector 114, without causing any back-up of filtered water. At the same time, the perforations must be small enough that gravel and sand cannot enter the interior of the assembly 136 and cause plugging.

Figure 16:
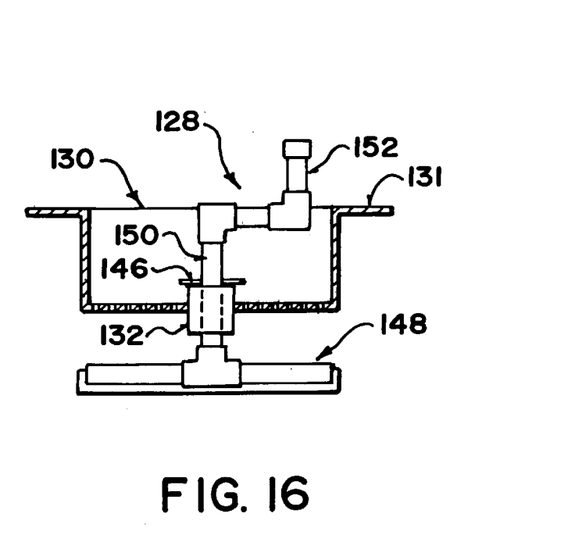
FIG. 16 is a side section view of the diffuser and clean in place apparatus according to the invention.

FIG. 16 illustrates a side section detail view of a diffuser basin 130 in combination with a mechanical agitator 128. The construction of the diffuser basin 130, rim 131 and bulkhead 132 has been explained previously. As seen in FIG. 16, the mechanical agitator 128 is constructed of a horizontal agitator blade 148 at the bottom thereof, a vertical shaft 150 extending upwardly from the centre of the agitator blade 148 through the bulkhead 132 of basin 130, with a manual horizontal winding handle 152 connected to the top end of the vertical shaft 150. The vertical shaft 150 is rotationally mounted in mechanical agitator bulkhead 132. Thus, the horizontal agitator blade 148 can be rotated in a clockwise or counterclockwise direction by manually winding handle 152. A height adjusting set pin 146 penetrates the shaft 150 and rests on the top of the mechanical agitator bulkhead 132 to keep the level of the blade 148 at a required elevation. In this way, the height of the mechanical agitator 128 and blade 148 can be held normally in a position above the top surface of the top sand layer 120 and the schmutzdeuke layer 119 (see FIG. 11). However, when the top surface of the top sand layer 120 and the schmutzdeuke layer 119 require cleaning, the height set pin 146 can be removed from shaft 150. This enables the agitator blade 148 to be lowered so that it reaches the top of top sand layer 120. Then, by manually winding handle 152 in a horizontal clockwise or counterclockwise direction, the operator causes the agitator blade 148 to rotate and scrape away a small portion of the top layer of the top sand layer 120. The thickness of the schmutzdeuke layer 119 builds up over time and retards water flow rate so periodic maintenance is required in order to maintain acceptable flow rates through the layer 119 and the sand layers 120, 122 and 124 of the intermittent slow sand filter.

Figure 17:
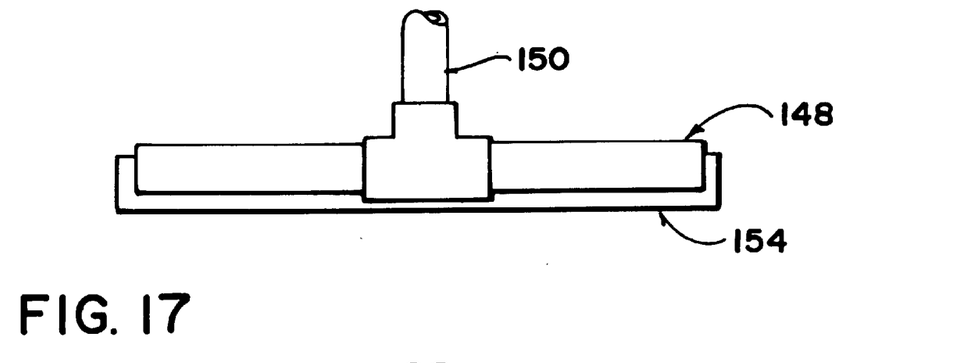
FIG. 17 illustrates a side view of a first design of agitation blade for the clean in place apparatus of FIG. 16.

FIGS. 17 through 22 illustrate different design embodiments of agitator blade 148. FIG. 17 illustrates in detail the design of the agitator blade 148 shown in FIGS. 12 and 16. Blade 148 has a rubber scraper 154 mounted on the bottom surface thereof. The rubber scraper 154 is similar in design to a window washing squeegee blade, and is stiff enough to scrape away a top layer of the top sand layer 120, but flexible enough to provide some yield.

Figure 18:
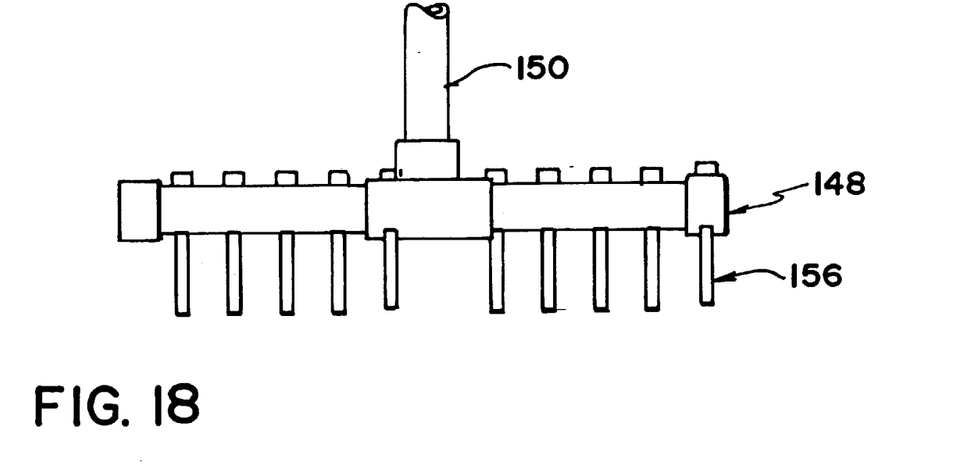
FIGS. 18 through 22 illustrate different alternative embodiments of agitation blades for the clean in place apparatus.

FIG. 18 illustrates an agitator blade 148 which has a series of vertical spaced scraper teeth 156 protruding vertically downwardly therefrom in a comb-like pattern. This arrangement provides a combing-action on the top surface of the sand layer 120, rather than a clean scraping action. The combing action may be desirable in instances where some of the top layer of the top sand layer 120 and the schmutzdeuke layer 119 is to be maintained.

Figure 19:
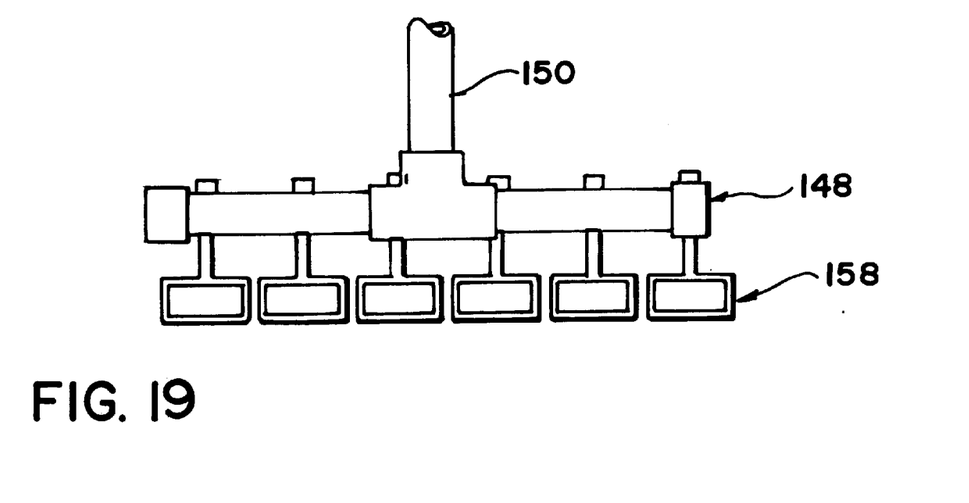

FIG. 19 illustrates a design of agitator blade 148 which has disposed along the bottom region thereof a series of scraper paddles 158. In some cases, the scraper paddles 158 may be preferred because the paddles 158 scrape most of the top layer of the sand 120, while at the same time permitting a certain amount of water to pass between the paddles 158. The horizontal angles of the paddles 158 can be adjusted to vary the size of the openings between adjacent paddles 158.

Figure 20:
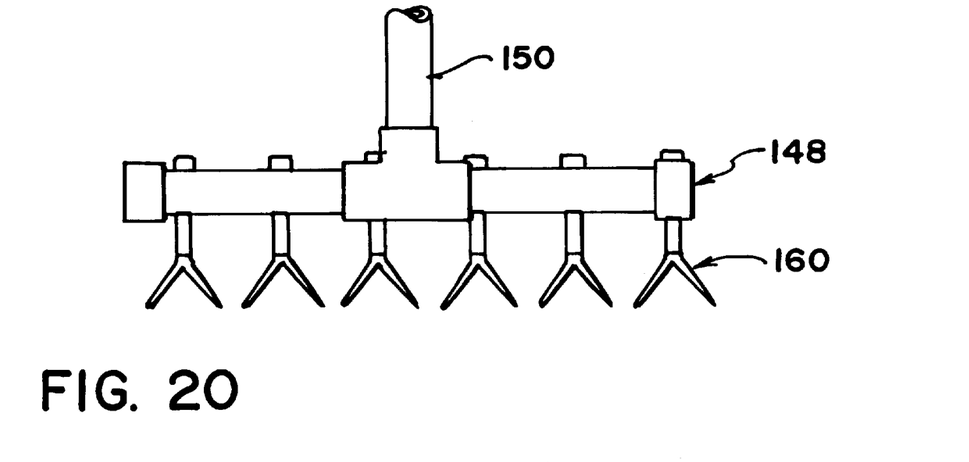
Figure 21:
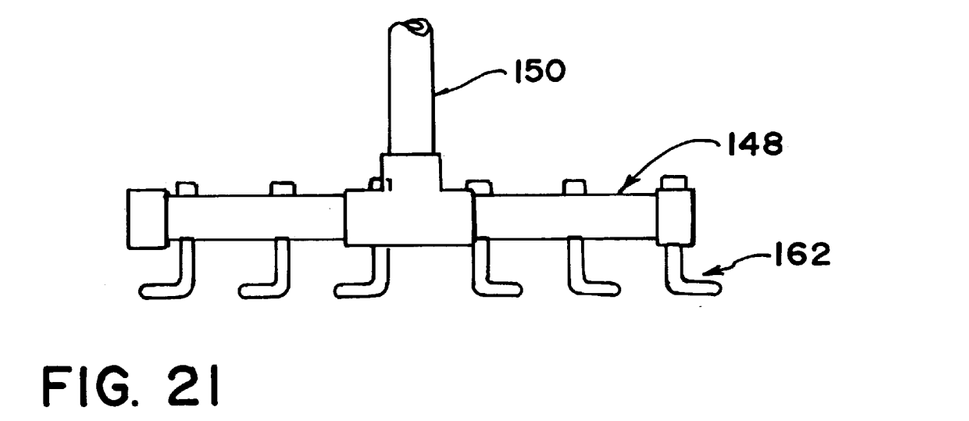
Figure 22:
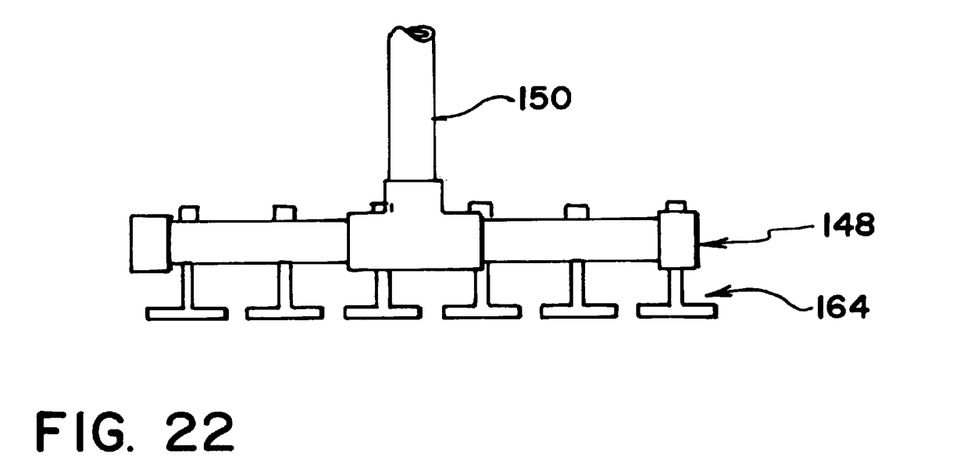

FIGS. 20, 21 and 22 illustrate respectively three different alternative designs of agitator blade 148. The design illustrated in FIG. 20 has a series of scraper forks 160 distributed along the bottom thereof. The design illustrated in FIG. 21 has a series of L-shaped scrapers 162 distributed along the bottom of the agitator 148. The design illustrated in FIG. 22 has a series of T-shaped scrapers 164 disposed along the bottom thereof. The horizontal angles of the various designs of scrapers 160, 162 and 164 can be adjusted to vary the size of the openings between the scrapers. Any of these alternative scraper designs can be selected to provide the type of scraping action that is required for specific situations.

Installation of Clean-in-Place Agitator Blade

The following instructions should be followed when installing the clean-in-place agitator blade 148.

(1) Turn off the flow of water to the container 102 by lifting the upper float switch in the treated water storage reservoir 62 (or close the ball valve on the inlet to the container 42 or 102).

(2) Disconnect the union inside the filter 42 or 102 and remove the mechanical float assembly, SHLA, SFP, STFP and ML.

(3) Remove the diffuser basin 64 or 130.

(4) Prepare a new diffuser basin for assembly. Attach the mechanical agitation blade 148 to the bottom of the centre shaft 150. Turn the male pipe threads into the female Tee connection. Attach the top portion of the handle 152 in a similar fashion.

(5) Set the new diffuser basin 130, with the agitator blade 148 and shaft 150, in place. Pull the centre shaft 150 up as far as possible and put the set pin 146 through the shaft 150 in the bottom position. This holds the mechanical agitator 148 above the top sand surface 120.

(6) Return the mechanical float assembly to the top of the filter. Tighten the union.

(7) Return the upper float switch in the treated water storage reservoir to its operating position. (Open the ball valve on the inlet to the container 102. This valve should be set at a position to reduce excess flow into the filter 102.)

Operation of Clean-in-Place Agitator Blade (1) Reference to FIGS. 9, 10 and 12 should be made for location of the valves when using clean-in-place agitator 128. It is recommended that the procedure should be done when the water level in the storage tank 62 is in the full range and the filter 102 is in the rest position.

(2) The procedure is commenced by closing the valve 76 at the treated water storage reservoir 62.

(3) The calibration valve 115 and the anti-siphoning valve 113 should be closed.

(4) The hose on the maintenance valve 109 is connected to the pressure tank 62 outlet. The valve at the pressure tank 62 is then slowly opened. The maintenance valve 109 is used to control the amount of flow into the filter 102. The flow rate of this back flow process should not need to be very forceful. Excess flow rates disturb and mix the bottom sand layers 122 and 124.

(5) The pin 146 is removed from the centre shaft 150 of the mechanical arm assembly 128. The agitation blade 148 is lowered to the top surface of the top sand 120. The pin 146 is inserted in the upper hole of the shaft 150.

(6) The mechanical arm is turned manually in either direction while the water level is slowly filling from the bottom. This mechanical agitation action will bring the particles on top of the filter surface 120 into suspension.

(7) Several buckets of water are drained off the top of top sand surface 120 using the drainage valve 116 at sand surface level.

(8) This process is continued until the majority of the suspended particles have been removed.

(9) The valves are then closed in the following order: the drainage valve 116, the valve 26 at the pressure tank, the maintenance valve 109.

(10) The following valves are then opened in the following order: the ball valve on the inlet to the container 102, the valve 81 at the treated water storage reservoir 62, and the calibration valve 115.

(11) The calibration valve 115 is set to 4 L/min. This is done by collecting water with a calibrated pail. The valve 115 is set so that 4 liters of water is collected in a one minute period, or an equivalent ratio can be used.

(12) The container 102 should now be restored to its original condition. This clean-in-place procedure as frequently as necessary to maintain the container filter 102 in optimum performance level.

Experimental Procedure and Results

Three prototype intermittently operated slow sand filters were assembled and installed in May, 1997. The filters were constructed such that the water depths above the surface of the sand in the filters, when they were paused, varied from 5 cm (recommended), 30 cm, and 100 cm. The filters were operated at least once every day until September, 1997. An assumption was made that the filters that were operated with the greater paused water depth would demonstrate characteristics similar to that observed by Paramasivan et al. and that the ones that were operated using a shallow water depth would demonstrate characteristics similar to that observed by Buzunis et al. Approximately four hours of technician time was required each time the filters were tested.

Water to be treated (artificially contaminated natural waste substitute) was produced in the laboratory using techniques which had been developed over the previous three years. This water was held in large tanks containing tropical fish and aquatic plants and was spiked periodically with small specified amounts of dog feces. This man-made waste water was used because it had very stable biological characteristics and was easy to produce in quantity.

The prototype filters were operated such that all of the water ponded on top of the sand in each case was replaced. Attempts were made to monitor the dissolved oxygen concentration in the water above the sand immediately prior to the addition of the new water. It was found that considerable time was required for each filter to accumulate sufficient organic matter at the sand surface for significant impacts on dissolved oxygen to be noted. It was ultimately determined that the techniques used to measure the dissolved oxygen were not sensitive enough. Though the techniques used were able to measure dissolved oxygen concentrations accurately, the techniques could not apparently be used to test the dissolved oxygen in the water immediately above the sand. This conclusion could not be reached until the experiment had been conducted for several months. This type of direct test for dissolved oxygen required miniature and specialized equipment. The results obtained were inconclusive as far as the objectives of the project were concerned. Nonetheless, we were able to demonstrate conclusively that we were able to operate the prototype slow sand filters on an intermittent basis and still maintain the schmutzdeuke in living condition.

Slow Sand Filter Construction—
Diffuser Plate Construction Detail

The three prototype slow sand filters were constructed of the following components:

filter container
filter cover
diffuser plate
pipe collector
washed 19 mm quartz gravel undrain
washed quartz sand (similar to that specified for continuous slow sand filters)
sand/gravel separation membrane
raw water supply intake
air vent
drain The three prototype filter containers were approximately 1000 mm in height and had a downwardly tapered variable cross-section. (In comparison, a filter for an individual household may be 400 mm in diameter.) The filter containers were constructed of PVC, concrete or any other material suitable for containing potable water could be used.

The filter covers were large enough to completely cover the filter top to prevent dust and other debris from accidentally entering the filter container.

The diffuser plates were required to spread the raw water supply evenly over the water in the filter, while it is at maintenance level, in such a fashion that turbulence was minimized and the water did not disturb the top surface of the sand or the schmutzdeuke layer. The diffuser plates were of a design that was capable of distributing the water at a rate greater than the raw water supplied to the filter container.

The filter underdrains at the bottoms of the three prototypes consisted of a layer of quartz gravel packed around a perforated PVC pipe collector.

The pipe collector in each prototype consists of a perforated 12 mm PVC pipe installed through the wall of the filter container. The holes in the PVC pipe were 3 mm in diameter and were located on the underside of the pipe. The pipe collector in each case was embedded in approximately 100 mm of 19 mm washed quartz gravel.

The filter sand in the prototypes consisted of washed quartz sand similar to that normally used for continuous flow slow sand filters. The sand layer was approximately 610 mm deep. As a performance criteria, the maximum rate of flow of water through the sand must be less than the minimum rate of flow of raw water flow to the filter.

The sand and gravel layers in the three prototypes were separated by a geomembrane.

Water was supplied to each of the filters through a raw water supply which delivered the water to the surface at the top of the diffuser plate. As a performance criteria, the raw water supply was located approximately 150 mm above the diffuser plate. The rate of flow through the raw water intake must be less than the rate of flow through the diffuser plate but greater than the maximum rate of flow of water through the filter sand.

The air vent and emergency drain in each prototype was provided at the very top of the filter container at the same elevation as the raw water intake. For satisfactory operation, the emergency drain must have the same capacity as the raw water supply. The air vent must be of sufficient capacity to allow air into the filter to escape during filling of the filter with water and to allow air to enter the filter during filter draining. (The air space at the tops of the filter must always be maintained at atmospheric pressure.)

A typical relationship of the slow sand filter to the raw water supply, potable water reservoir and potable water distribution system is shown in the schematic illustrated in FIG. 7. Water is pumped into the filter from the raw water supply. If the raw water reservoir is elevated above the filter, the feed pump may be replaced by a solenoid valve.

Water drains from the slow sand filter into the potable water reservoir through a piping system which includes a ball valve, union, solenoid valve and another union. Under emergency conditions, water may be drained from the filter into the raw water supply or to waste through the emergency drain. The potable water reservoir of the prototype was sized to contain a water supply sufficient for normal use. Potable water was supplied to the potable water distribution system through a distribution system pump.

In the prototypes, the distribution system, including the pump, is isolated from the reservoir by a ball valve and union. Another union is located immediately downstream of the pump. A tee in the piping is located downstream of this union. One outlet of the tee provides water as required to the potable water distribution system. The other outlet is controlled by a solenoid valve which is operated when it is necessary to freshen the filter. When this valve is open, water from the potable water reservoir is returned to the raw water reservoir.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A slow sand filter apparatus capable of being operated intermittently comprising:
    a container having an upper portion and a lower portion;
    a water inlet in the upper portion of the container, the water inlet being connected to a supply of water;
    a first layer of filter material in the lower portion;
    a second layer of filter material above the first layer filling at least the lower portion of the container, the second layer of filter material having a top surface below the water inlet;
    a schmutzdeuke layer on the top surface of the second layer of filter material;
    a perforated diffuser below the water inlet and above a water maintenance level, the water from the water inlet passing through the perforations in the diffuser before reaching the top of the water maintenance level and the underlying second layer of filter material;
    a water outlet in the lower portion of the container below the top surface of the second layer of filter material; and
    a water level maintenance device which maintains water in the upper portion of the container at a maintenance level between about 1 cm and 8 cm above the top surface of the schmutzdeuke layer and the second layer of filter material, the maintenance level device comprising
    a first water level detector to detect an upper water level in the container;
    a second water level detector to detect a lower water level in the container; and
    a programmed microprocessor connected to receive signals from the first and second container water level detectors and to provide signals to a water inlet control means, so that the water maintenance level is maintained between (1) a water maintenance level that is sufficiently deep that water falling from the water inlet through the diffuser onto the top of the water in the container does not significantly disturb the schmutzdeuke layer; and (2) a water maintenance level that is sufficiently shallow that oxygen from the air above the water level can diffuse through the water and reach the schmutzdeuke layer so that the schmutzdeuke layer is maintained in living condition even when there is no flow of water through the water inlet.

2. The slow sand filter apparatus of claim 1 wherein the water level maintenance device includes a pipe connected to the water outlet and extending upward to the water maintenance level.

3. The slow sand filter system of claim 2 wherein the second layer of filter material is quartz sand.

4. The slow sand filter apparatus of claim 1 wherein the water level maintenance device maintains the water level between about 1 cm and 5 cm above the top of the filter material.

5. The slow sand filter apparatus of claim 1 including a water inlet line connected to the water inlet and water inlet control means for controllably supplying water to the water inlet line.

6. The slow sand filter apparatus of claim 1 wherein the diffuser has the shape of a basin and includes discrete holes which allow water accumulating in the diffuser to percolate down through the holes in the diffuser onto the top of the water in the container.

7. The slow sand filter apparatus of claim 1 further including:
    a water reservoir connected to the water outlet;
    first and second water reservoir water level detectors for detecting high and low water levels in the water reservoir; and
    a flow control for controlling flow of water from the water outlet of the container into the water reservoir.

8. A slow sand filter apparatus of claim 7 including a raw water reservoir connected to the water inlet of the apparatus and a control for controlling flow of water from the raw water reservoir to the sand filter apparatus.

9. The slow sand filter apparatus of claim 8, including:
    a water inlet control for controlling flow of water to the water inlet.

10. The slow sand filter apparatus as claimed in claim 1 including a mechanism which enables a top surface of the second layer of filter material to be cleaned.

11. The slow sand filter apparatus as claimed in claim 10 wherein the cleaning mechanism is a manually operatable mechanical agitator.

12. The slow sand filter apparatus as claimed in claim 11 wherein the mechanical agitator comprises an agitator blade, which contacts the top surface of the filter material, and a rotatable shaft and handle which can enable the agitator to be manually rotated.

13. The slow sand filter apparatus as claimed in claim 12 wherein the agitator blade includes a member selected from the group consisting of a scraper blade, scraper teeth, scraper paddles, scraper forks, L-shaped scrapers and T-shaped scrapers.

14. The slow sand filter apparatus as claimed in claim 13 wherein the mechanical agitator is journalled for rotation in the water diffuser which is located in the upper portion of the container.

15. A method of operating a slow sand filter, the filter including a container, filter material partially filling the container, a water inlet above the filter material and a water outlet within the filter material, a schmutzdeuke layer on the filter material, a perforated diffuser above the filter material, and a programmed microprocessor, the method comprising the steps of:

introducing water into the container above the filter material through the perforated diffuser and using a programmed microprocessor to maintain a water level in the container above the top of the filter material at a level which is a balance between (1) a water maintenance level that is sufficiently deep that water falling from the water inlet through the perforated diffuser onto the top of the water in the container does not significantly disturb the schmutzdeuke layer; and (2) a water maintenance level that is sufficiently shallow that oxygen from the air above the water level can diffuse through the water and reach the schmutzdeuke layer so that the schmutzdeuke layer is maintained in living condition even when there is no flow of water through the water inlet.

16. The method of claim 15 wherein the water level is maintained at between 1 cm and 8 cm above the top of the filter material.

17. The method of claim 15 wherein the water level is maintained at between 1 cm and 5 cm above the top of the filter material.

* * * * *